(12) United States Patent
Versi

(10) Patent No.: US 8,029,496 B2
(45) Date of Patent: Oct. 4, 2011

(54) METHOD AND DEVICE FOR DELIVERING DRUG TO THE TRIGONE OF THE BLADDER

(76) Inventor: Ebrahim Versi, Gladstone, NJ (US)

( * ) Notice: Subject to any disclaimer, the term of this patent is extended or adjusted under 35 U.S.C. 154(b) by 0 days.

(21) Appl. No.: 12/231,532

(22) Filed: Sep. 3, 2008

(65) Prior Publication Data
US 2009/0171315 A1 Jul. 2, 2009

(51) Int. Cl.
*A61M 31/00* (2006.01)
(52) U.S. Cl. ........................................ 604/511
(58) Field of Classification Search .......... 604/506, 604/544, 581, 19, 131, 272–274, 511; 607/99, 607/113
See application file for complete search history.

(56) References Cited

U.S. PATENT DOCUMENTS 5,354,279 A * 10/1994 Hofling ................. 604/164.12
5,749,845 A * 5/1998 Hildebrand et al. ............ 604/21
6,692,490 B1 * 2/2004 Edwards ........................ 606/41
2007/0038181 A1 * 2/2007 Melamud et al. ............. 604/158

* cited by examiner

*Primary Examiner* — Theodore Stigell
*Assistant Examiner* — Imani Hayman

(57) ABSTRACT

Methods of treating functional disorders of the bladder in mammalian females are disclosed. A therapeutic compound is delivered directly into the trigone of the bladder. The therapeutic may be delivered to the trigone through the vaginal wall. A device for delivering the therapeutic compound is also disclosed. The device may be an array of microneedles connected to a reservoir.

3 Claims, 2 Drawing Sheets

METHOD AND DEVICE FOR DELIVERING DRUG TO THE TRIGONE OF THE BLADDER

This application claims priority of U.S. Application No. 60/779,010, filed Mar. 3, 2006.

BACKGROUND OF THE INVENTION

The present invention relates to a method and device for treating functional bladder disorders and related disorders in women by administering a therapeutic composition to the trigone of the bladder through the vagina.

The bladder functions to store urine and at appropriate times under voluntary control to void urine and hence empty to completion in an efficient and timely manner. The storage and voiding functions of the bladder are under neural control. The innervation of the bladder is primarily autonomic with the parasympathetic system thought to dominate during voiding and the sympathetic system dominating during the storage phase. However the innervation of the bladder is complex and many of the mechanisms of storage and voiding are poorly understood. In particular there is much local interplay of complex neuronally active molecules especially related to the sensory mechanisms.

Functional disorders of the bladder interfere with the normal storage or voiding functions. Many of the functional disorders of the bladder can be treated pharmacologically. Most treatments of functional disorders are systemic with the resultant adverse effect due to pharmacological action in other body systems. Local therapy has been carried out by injection into structures of the bladder by direct visualization of the internal structure of the bladder through a cystoscope. While this method allows accurate anatomic placement of the therapeutic agent, it does require expertise in cystoscopy, consequently limiting the number of healthcare providers who can administer this type of therapy.

Local therapy would be preferred as it would avoid adverse events from distal systems at risk from systemic therapy and would allow the use of therapeutic agents that would otherwise be toxic if administered systemically. The neuronal supply to the bladder is profuse at the neck of the bladder, near the region known as the trigone. Consequently, this is an ideal site for local administration of therapeutic agents. However, local administration of drug to the bladder has been limited by the need to use a cystoscope. To date, the trigone has not been accessed via the vagina for the purposes of pharmacological treatment. The present invention provides a novel method and device for accessing the trigone for local application of therapeutic compounds to the bladder.

SUMMARY OF THE INVENTION

The present invention provides a method of treating a functional disorder of the urinary bladder of a female patient comprising administering a therapeutically effective amount of a compound for treating the disorder through the vaginal wall of the patient into the trigone of the urinary bladder. In a preferred embodiment, the administration is by injection through the vaginal wall with at least one needle. In another preferred embodiment, infection is done with a plurality of needles.

The present invention also provides a device for delivering a fluid into the trigone of the urinary bladder comprising an array of needles in fluid-receiving connection with a reservoir. The needles in the array are of a sufficient length to extend through the vaginal wall into the trigone. The needles are in fluid receiving connection to a reservoir, which may contain any therapeutic compound of choice. The reservoir may be adjacent to the needle array. Alternatively, the reservoir may be connected to the needle array by a conduit, such as a catheter, so that the reservoir may remain outside the body of the patient while the needle array is placed within the vagina.

DETAILED DESCRIPTION OF THE INVENTION

Figure 1:
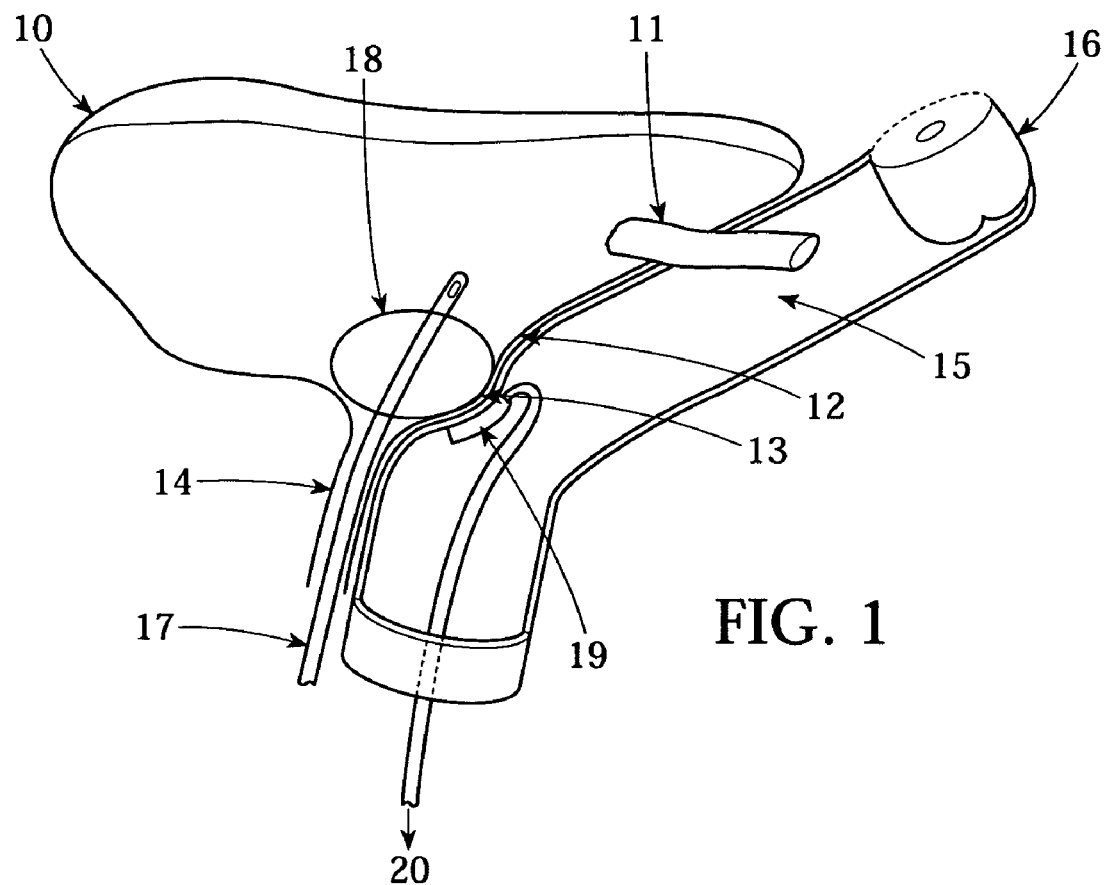
FIG. 1 is a schematic sagittal view of the bladder, urethra, part of the ureter as it enters the bladder, vagina and the lower portion of the cervix. A Foley catheter with inflated balloon is shown in place in the bladder defining the urethro-vesical junction. A needle array is shown in place in the vagina with its leading edge at the urethro-vesical junction. From the needle array a conduit is shown leading to a reservoir which is not shown.

The present invention provides a method for treating functional disorders of the urinary bladder in women comprising administering a therapeutically effective compound into the trigone of the urinary bladder, which is anatomically adjacent and intimate to the vagina. The therapeutic compound is administered through the vagina wall into the trigone.

Functional disorders of the bladder include urinary incontinence, overactive bladder, unstable bladder, detrusor instability, detrusor over activity, detrusor hyperreflexia, urethral instability syndromes, interstitial cystitis, sensory urgency, painful bladder syndrome, radiation cystitis, detrusor hyporeflexia and detrusor sphincter dyssynergia and urinary retention. Symptoms of these conditions may include urinary incontinence, urinary urgency, urinary frequency, nocturia or noctural urinary frequency, urinary retention, voiding difficulty, difficulty in initiating a urinary stream, bladder pain, bladder pressure, intermittent urinary stream, poor urinary flow, postmicturition dribbling, and incomplete emptying.

Therapeutically effective compounds useful in the present invention include, without limitation, neurotoxins such as botulinum toxin or modifications of such molecules, muscarinic receptor antagonists, muscarinic receptor agonists spasmolytics, antidepressants, adrenoreceptor alpha antagonists, adrenoreceptor alpha agonists, adrenoreceptor beta antagonists, adrenoreceptor beta agonists, adrenoreceptor beta-3 agonists, cyclo-oxygenase inhibitors, vanilloid receptor agonists, vanilloid receptor antagonists, purinergic receptor antagonists, purinergic receptor agonists, tachykinin receptor agonists, tachykinin receptor antgonists, vasoactive peptide receptor agonists, vasoactive peptide receptor antagonists, opioid receptor agonists, opioid receptor antagonists, and compounds that enhance or inhibit or modulate nitric oxide synthesis.

The two primary functions of the bladder, namely storage and voiding, are mechanistically in many ways opposite to each other. As such, drugs used to treat these functional disorders may also have opposite actions. Therefore for one condition an antagonist would be used whereas its agonist would be used for its opposite function. An example of this is overactive bladder and detrusor hypotonia. For the former an antimuscarinic agent would be used while for the latter, a muscarinic agonist would be used.

A therapeutically effective amount of the drug is the dosage sufficient to exhibit activity for at least one week, more preferably one month, most preferably for approximately 6 to 8 months or longer. Dosing can be single dosage or cumulative (serial dosing), and can be readily determined by one skilled in the art. Drug can be delivered serially (i.e., one time per month, one time per every six months) so that the therapeutic effect can be optimized and maintained. Such a dosage schedule is readily determined by one skilled in the art based on, e.g., patient size and the condition to be treated, and will depend on many factors, including the drug selected, the condition to be treated, the severity of the disease, and other variables.

Therapeutic compounds may be administered individually, or may be administered in combination with other therapeutic compounds to treat one or even more than one disorder simultaneously. When administered in accordance with the methods and device of the present invention, such combinations of therapeutic compounds enable treatment of a single or multiple bladder disorders in a single procedure and with fewer visits to a health care provider.

Botulinum toxin has been used to inhibit release of neurotransmitter from the nerve terminals. Some studies advocate its use in patients with detrusor hyperreflexia, the goal being to paralyze the bladder and allow clean intermittent self catheterization (CISC) to be employed for bladder emptying. The paralysis is achieved by injecting all over the bladder, sparing the trigone based on the theoretical notion that a trigonal injection may impair ureteric emptying. This degree of morbidity necessitating the use of CISC is acceptable in patients with detrusor hyperreflexia. Similar regimens have been advocated for the treatment of overactive bladder but using a lower dose of botulinum toxin to reduce the urinary retention rate. However, for this less serious condition, any degree of retention or increase in post void residual urine volume is unacceptable as this can lead to additional clinical problems such as an increased susceptibility to urinary tract infection. Injecting all over the bladder results in paralysis of the detrusor muscle even when voiding is required. There is a growing body of evidence suggesting that overactive bladder has its etiology in the afferent arm of the neural control of bladder function. If this is correct, then paralysis of the detrusor muscle is not a logical therapeutic approach. Most of the sensory afferents to the bladder traverse through the trigone and the trigone plays no significant role during bladder emptying. Limiting the injections to the trigone is more logical as it would remove voiding dysfunction as a side effect of therapy.

The use of the neurotoxins is especially amenable to administration in accordance with present invention because of their long-lasting inhibition of synaptic function, preferably greater than one week, more preferably greater than one month, most preferably six to eight months or longer. Such neurotoxins can include, for example, capsaicin, resiniferatoxin, a-bungotoxin, terodotoxin and botulinum toxin. Botulinum toxin has in the past been injected into the bladder via the cystoscope. The technique of the present invention utilizing a needle patch does not require cystoscopy and therefore considerably reduces the complexity of and the degree of expertise required for the procedure.

The toxin can also be used in any pharmaceutically acceptable form supplied by any manufacturer. The dosages can be given as a single dose, or as divided doses, for example, divided over the course of four weeks. The treatment can be repeated as necessary determined by recurrence of symptoms. The drug may be administered in any pharmaceutically acceptable formulation such as a liquid, a suspension, or a solution.

The aforementioned methods of treatment should be particularly useful for the long-term control of functional disorders of the bladder, e.g., overactive bladder or interstitial cystitis. Furthermore, the methods of the instant invention provide for control of functional disorders of the bladder, e.g., overactive bladder and related conditions, in a highly selective manner, without the potential side effects and treatment failures associated with current treatment modalities.

Anatomically, the bladder consists of two regions. Its lower region contains the trigone, a triangular area whose upper vertices on the right and left are marked by the entry points of the respective ureters, which transport urine into the bladder from the kidneys. The third, more forward vertex of the trigone is the point at which the urethra exits the bladder. The size, shape and relationship of the bladder to surrounding structures vary with its urine content. Because it is essentially fixed by endopelvic fascia to the underlying vaginal wall, the position of the trigone of the bladder changes little in its relationship to the vagina as the bladder fills with urine. However, as the bladder fills, its remaining distensible portion, the fundus, can rises from the pelvis, protruding into the abdominal cavity when the bladder is maximally distended.

The bladder is innervated by the autonomic nervous system, the sympathetic drive predominating during bladder filling and the parasympathetic system during bladder emptying. Sensations from the bladder to the spinal cord and brain usually run with the branches of the sympathetic nerves. The parasympathetic innervation of the bladder provides motor stimuli to the bladder (detrusor) muscle and, when activated by voluntary or involuntary control, cause contraction of the detrusor and possibly relaxation of the sphincter muscles of the urethra, thereby promoting the expulsion of urine from the bladder. In contrast, the sympathetic innervation inhibits contraction of the detrusor and promotes contraction of the urinary sphincters, restricting the excretion of urine.

The trigone contains a higher concentration of nerves relative to the rest of the bladder wall. The trigone thus provides an ideal site for localized administration of therapeutic compounds to the bladder.

The present invention provides a method for treating a functional disorder of the urinary bladder whereby the compound is delivered into the urinary bladder trigone through the vaginal wall. In a preferred embodiment, the compound is injected into the trigone through at least one needle inserted through the vaginal wall. In another preferred embodiment, the compound is injected into the trigone through a plurality of needles inserted through the vaginal wall.

Microneedle arrays or patches have been developed for various uses in drug administration and biological sample collection. The use of microneedle arrays is well-known for the transmembrane administration of drugs. Microneedles have been developed to enable transdermal delivery of drugs without pain or bleeding, due to the shortness of the needles which do not extend deep enough into the skin to contact nerves or capillaries. The needle array of the present invention is larger than the microneedle arrays previously disclosed but similar manufacturing techniques could be used or modified for the present invention. Needle arrays of the present invention may be manufactured by any of various well-known methods, such as injection molding, masking and etching techniques, or laser etching techniques. (See, e.g., Proceedings of SPIE—Volume 4936; Nano- and Microtechnology: Materials, Processes, Packaging, and Systems, Dinesh K. Sood, Ajay P. Malshe, Ryutaro Maeda, Editors, November 2002, pp. 113-118. See also, for example, U.S. Pat. No. 7,132,054. These publications are hereby incorporated by reference into the present application.)

The present invention provides a device for delivering a fluid into the trigone of the urinary bladder comprising an array of needles in fluid-receiving connection with a reservoir. In a preferred embodiment, the needle array is substantially triangular, corresponding to the shape of the trigone.

In a preferred embodiment, the array of needles comprises a plurality of needles of varying length within range of about 2-20 millimeters, to account for the different thickness of the anterior vaginal wall in different women, in fluid-receiving connection with a reservoir.

In another embodiment the needles in the array in any one device have substantially the same length. Several different devices each with a different length of needle are available for use with different patients. The physician determines the appropriate device to use on an individual patient by measuring (sizing) the thickness of the vaginal-bladder wall beneath the trigonal urothelium. If the needle length is too long, the tip would perforate through the urothelial lining and the therapeutic compound would be injected into the lumen of the bladder. Depending on the therapeutic agent being administered, this might result in ineffective or undesirable effects but with some agents (eg: botulinum toxin), it could still have a therapeutic effect.

Figure 4:
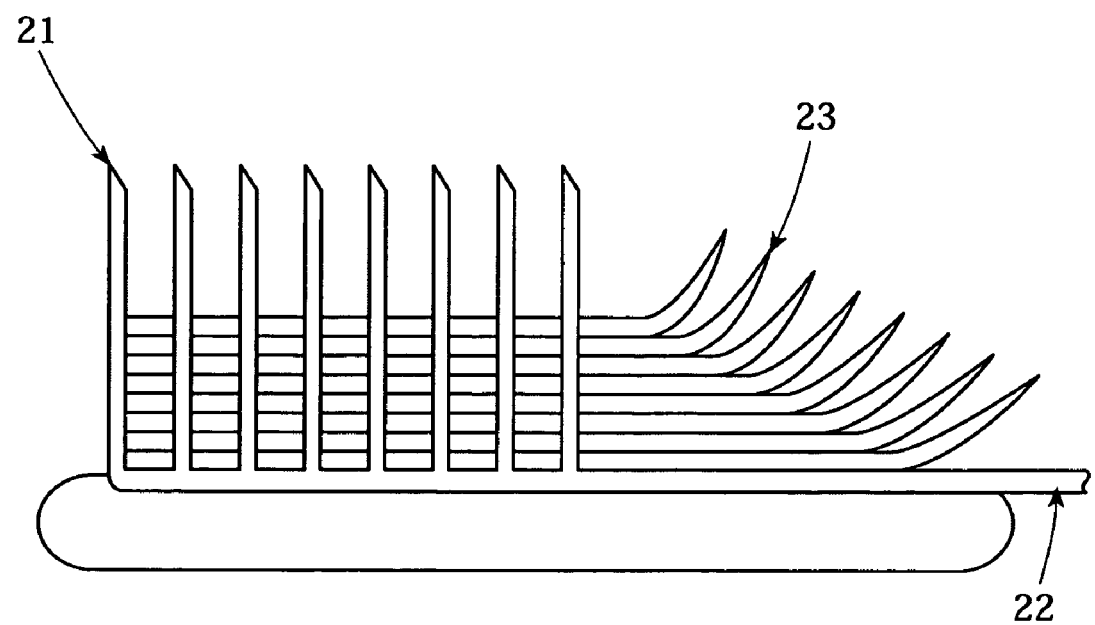
FIG. 4 is an elevation view of a needle array showing needles extending through removable layers of material which may be removed to expose a desired length of the needles.

In another embodiment the needles in the array in any one device have substantially the same length but greater than that required. The actual length of the needles that are exposed prior to application could be adjusted by peeling off the appropriate number of protective layers after the patient has been sized (FIG. 4).

In another embodiment, the device further comprises a conduit connecting the array of needles and the reservoir. The conduit is of any suitable length sufficient to allow for the reservoir to remain outside of the patient's body, for ease of manipulation by the physician. In a preferred embodiment, the conduit can be of varying length within the range of 2-30 centimeters in length. In another preferred embodiment the reservoir could be directly connected to the device without the need for a conduit.

In another embodiment the connection of the conduit to the needle patch can be molded fused and the conduit could be molded fused to the reservoir. The reservoir would be preloaded with the therapeutic agent and the whole sterilized and maintained so in a sealed sterile pack prior to opening immediately before the procedure.

In another embodiment the conduit would be detachable from the needle patch and from the reservoir or syringe containing the therapeutic agent. This would allow the needle patch to be used for a variety of therapeutic agents.

In another embodiment the connection from the conduit to the needle patch could be fused but the connection from the reservoir or syringe containing the therapeutic agent could be detachable.

In another embodiment the connection from the conduit to the needle patch could be detachable but the connection from the reservoir or syringe containing the therapeutic agent could be fused.

In another embodiment the needle patch is connect directly to a syringe or similar deliver mechanism. In this way once the patch is position in place the therapeutic agent can be injected into the trigone by pressure on the plunger of the syringe.

In another embodiment, the conduit further comprises a one-way valve which permits the flow of fluid from the reservoir to the array of microneedles and prevents flow from the array to the reservoir.

The present invention further provides a kit which comprises a Foley catheter and a substantially triangular array of microneedles in fluid-receiving connection with a reservoir.

The whole package could be prepared and sterilized and contained in a sterile package prior to use or it could be sterilized immediately prior to use. The therapeutic agent could be packed with the kit or dispensed separately.

The distance between the mucosal lining of the anterior vaginal wall and the urothelium overlying the bladder trigone may vary between individuals. This distance can be measured in cadavers but the measurements may not reflect the in vivo situation because of post mortem changes. At surgery such measurements can be made but the area is often infiltrated with saline, local anesthetic or a vasoconstrictor agent or other fluid prior to the anterior vaginal wall to aid dissection. These maneuvers would also distort the tissue revealing inaccurate measurements. The distance between the mucosal lining of the anterior vaginal wall and the urothelium overlying the bladder trigone may be accurately measured by transvaginal ultrasound scanning. Such data has not been published but extensive anecdotal reports by experts in the area agree that this distance is about 7 mm. However there is individual patient variation. The vaginal mucosa thins with age and is thinner in post-menopausal women who do not receive estrogen therapy but the average thickness is about 3 mm. The bladder wall at the trigone is about 3.5 mm thick but has been shown to be slightly thicker in patients with detrusor instability. Thus distance between the external vaginal mucosa and the internal trigonal urothelium is about 8 mm in women with detrusor instability. Such small intra-patient variations do not make a material difference to the method of use of this invention, but sizing of this distance may be of clinical utility and hence is incorporated in embodiments of the invention.

Sizing can be done in a variety of ways but one technique is with the use a needle fixed to an empty syringe that is inserted perpendicular to the vaginal wall at the level of the trigone. For this technique to be performed, the bladder needs to contain a minimal amount of urine. As the needle is slowly pushed through the vaginal wall, suction is applied to the syringe. As soon as urine is seen to flow into the syringe, the needle is withdrawn slightly until the urine flow stops. As the thickness of the vaginal-bladder wall complex at the level of the trigone may vary between individuals, this technique can be used to determine the length of the needle required to penetrate to the trigonal sub-urothelium. The physician then marks the needle at the point at which it enters the vaginal wall. This may be done, for example, by sliding a site marker up the shaft of the needle until it rests next to the vaginal wall. In another technique the physician places his/her finger on the shaft of the needle with the tip of the finger at the point where the needle enters the vaginal wall. In this manner, once the needle is withdrawn, the length of the needle required to reach the sub-urothelium at the level of the trigone can be determined. This can then be used to choose the appropriate device for that individual patient.

In another embodiment, sizing could be performed by using the needle array patch itself. The needle array patch can be appropriately sited and fluid can be injected through a syringe attached to the patch in place of a reservoir or via a conduit. Based on the pressure required to inject the fluid, someone practiced in the art would be able to judge if the needles are too long and protruding into the bladder lumen. To aid with the pressure assessment, a simple manometer or gauge could be attached to the conduit to measure the pressure as fluid is pushed through the needles in the patch. If the needles are deemed to be too long for that particular patient, a patch with a shorter needle array is used.

In one embodiment of the invention, the needle array lengths are substantially the same, measuring any length in excess of that required to penetrate to the sub-urothelium of the trigone, but short enough so as not to extend into the bladder cavity itself.

In a preferred embodiment this would be between 2 and 20 millimeters. The needle array may be constructed and packaged so that the needles pierce through several separate layers of soft pliable protective material of uniform thickness. As shown in FIG. 4, individual layers of the material (23) may be removed successively to expose the tip of the needles (21). The removal of more layers exposes more of the length of the needles. In a preferred embodiment of the device, these layers would be made of a non-allergic material such as silicone and their thickness would be 1 millimeter each. After the vagina-bladder wall thickness of an individual patient has been sized, the appropriate number of layers of the protective material is peeled off leaving the exposed length of the needles appropriate for the patient.

Once the appropriate patch and needle size has been determined, the patch is applied to the anterior vaginal wall at the level of the trigone as determined by the location of the Foley balloon (see FIG. 1). The patch is fully pressed on to the vaginal wall so that the needle tips are located in the sub-urothelial space and the therapeutic agent is injected.

Prior to insertion of a needle(s) into the trigone for sizing or injection of therapeutic agent(s), the area could be anesthetized with a local anesthetic such as lidocaine as this part of the bladder is particularly sensitive. In another embodiment, the needle array patch itself is used to infiltrate the trigone with a local anesthetic prior to injecting the therapeutic agent. The technique for the anesthetic injection would be similar to that for injecting the therapeutic agent, using a ready filled reservoir or a syringe filled with the local anesthetic such as lidocaine.

FIG. 1 shows the bladder (10) and a ureter (11) entering the bladder (10). The inter-ureteric ridge (12) lies between the entry points of ureters (11) into the lumen of the bladder (10). The trigone (13) is the area of the bladder wall bounded by the entry points of the ureters (11) and the exit point of the urethra (14). The vagina (15) lies adjacent, just inferior and posterior, to the bladder (10). The tip of the cervix (16) is shown at the end of the vagina (15). In this schema, the uterus is not shown.

In the method of the invention, the area of the vaginal wall adjacent to the trigone (13) may be located by use of a Foley catheter (17) inserted into the urethra (14). The Foley catheter (17) has a balloon (18) at its distal end. With the catheter balloon (18) inflated, the catheter is gently withdrawn until its movement is arrested as the balloon abuts against the bladder neck, as shown in FIG. 1. In this position, the balloon (18) is located upon the trigone (13). The area of the vaginal wall adjacent to the trigone (13) may then be located by palpating the location of the balloon (18) from within the vagina (15). This are can then be marked with a surgical marker pen to ensure that the needle array patch is appropriately sited. This procedure provides a quick, easy office procedure with minimal discomfort to the patient.

Figure 2:
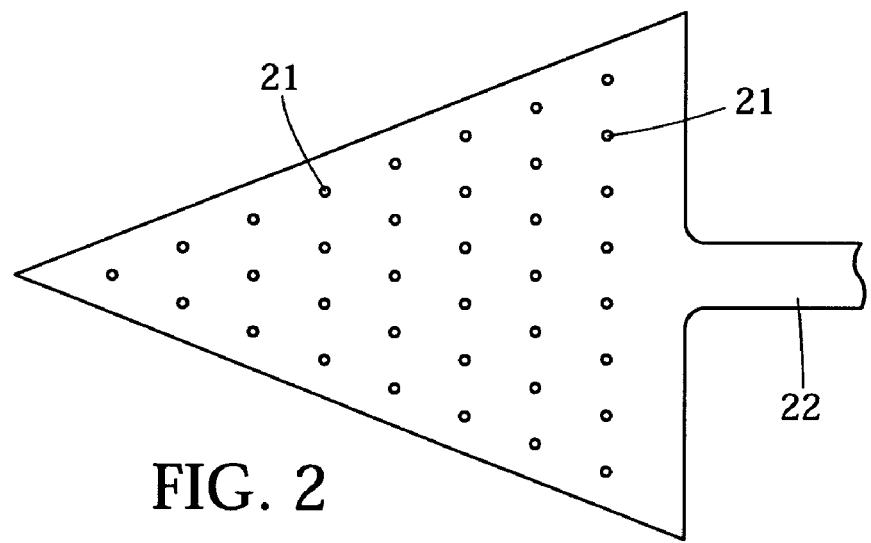
FIG. 2 is a plane view of the device showing the needle array and part of the conduit leading to the reservoir, which is not shown. The triangular shape of the needle array mirrors the shape of the trigone.
Figure 3:
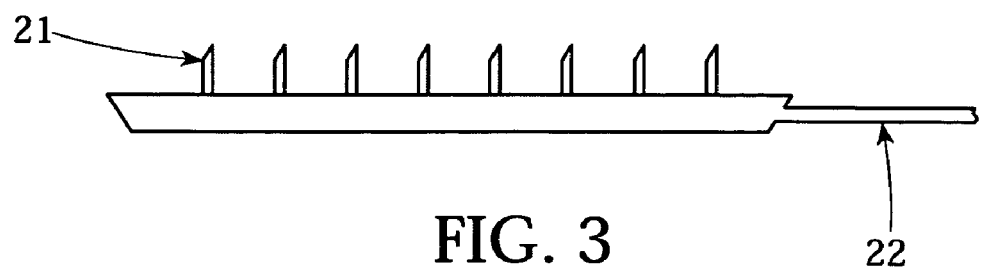
FIG. 3 is an elevation view of the device showing the needle array and part of the conduit that leads to the reservoir.

After the area of the vagina (15) adjacent to the trigone (13) is thus located, a therapeutic compound may be administered through the vaginal wall into the trigone (13). Therapeutic compound may be administered by any means which enables the compound to traverse the vaginal wall and contact the trigone. In one embodiment, therapeutic compound may be injected through the vaginal by use of a needle and syringe. In another embodiment of the invention, a needle array (19) having a plurality of needles (21), as shown in FIGS. 2 and 3, may be used to administer the compound through the vaginal wall adjacent to the trigone (13). The needles (21) are of sufficient length to extend through the vaginal wall and into the trigone (13). The length of the needles may vary between devices or within a single device. The length of needles may easily be selected to suit an individual patient. In a preferred embodiment, the length of the needles (21) is at least about 2 millimeters, and preferably is in the range of about 2-20 millimeters. In a particularly preferred embodiment, the length of the needles (21) is in the range of about 4-12 millimeters. In another particularly preferred embodiment, the length of the needles (21) is in the range of about 6-8 millimeters. The needle array (19) is connected to a reservoir containing the therapeutic compound in fluid form. When pressure is applied to the reservoir, the fluid is expelled through the needles in the array, through the vaginal wall, and into the trigone (13). In one embodiment, the reservoir may be directly connected to the needle array (19) and separated by a barrier that retains the compound in the reservoir until pressure is applied. Application of pressure breaches the barrier and forces fluid containing the compound out of the reservoir, and into and through the needles in the array. In another embodiment, the reservoir is connected to the needle array (19) by means of a conduit (20). The conduit (20) is of sufficient length to extend outside of the vagina when the needle array (19) is disposed on the vaginal wall adjacent to the trigone (13). The reservoir thus remains outside the vagina while the needle array (19) is in place on the vaginal wall adjacent to the trigone (13). In this configuration, the expulsion of fluid from the reservoir may be more easily controlled.

Various means may be employed to transfer fluid containing therapeutic compound from the reservoir. Expulsion of fluid may be effected by, for example, mechanical compression of the reservoir, electronic metering, vacuum, and other well known means. Any of various devices may be adapted to function in the present invention, such as, for example, a syringe, pump, or a compressible bulb. Operation of the means for expelling fluid may be controlled by various mechanisms, for example, mechanical or electronic.

The foregoing description of the invention is exemplary for purposes of illustration and explanation. It will be apparent to those skilled in the art that changes and modifications are possible without departing from the spirit and scope of the invention. All of the various publications cited herein are hereby incorporated by reference.

What is claimed is:

1. A method for administering a fluid into the trigone of the urinary bladder of a female patient comprising the steps of:
   i) placing at least one needle which is in fluid-receiving connection with a reservoir containing a fluid into a vagina;
   ii) inserting the needle through a vaginal wall into a trigone; and
   iii) activating a fluid expulsion means for injecting the fluid through the needle into the trigone.

2. The method of claim 1, wherein the administering comprises injection through a plurality of needles inserted through the vaginal wall into the trigone.

3. The method of claim 2, wherein the administering comprises injection through a patch bearing an array of needles.

* * * * *